US009697328B2

(12) United States Patent
Ranatunga

(10) Patent No.: US 9,697,328 B2
(45) Date of Patent: Jul. 4, 2017

(54) TRANSMISSION APPARATUS, TRANSMISSION METHOD, RECEPTION APPARATUS, RECEPTION METHOD, AND COMPUTER PROGRAM

(71) Applicant: Sony Corporation, Tokyo (JP)

(72) Inventor: Sanjeewa Ranatunga, Kanagawa (JP)

(73) Assignee: Sony Corporation, Tokyo (JP)

(*) Notice: Subject to any disclaimer, the term of this patent is extended or adjusted under 35 U.S.C. 154(b) by 550 days.

(21) Appl. No.: 14/063,096

(22) Filed: Oct. 25, 2013

(65) Prior Publication Data

US 2014/0118618 A1    May 1, 2014

(30) Foreign Application Priority Data

Nov. 1, 2012   (JP) ................. 2012-241528

(51) Int. Cl.
| H04N 7/12 | (2006.01) |
| H04N 11/02 | (2006.01) |
| H04N 11/04 | (2006.01) |
| H03M 13/00 | (2006.01) |
| H03M 13/03 | (2006.01) |
| G06F 19/00 | (2011.01) |
| H04L 29/06 | (2006.01) |
| G06Q 50/22 | (2012.01) |
| H04N 7/18 | (2006.01) |

(52) U.S. Cl.
CPC ........ *G06F 19/321* (2013.01); *G06F 19/3418* (2013.01); *G06F 19/3481* (2013.01); *G06Q 50/22* (2013.01); *H04L 65/80* (2013.01); *H04N 7/18* (2013.01)

(58) Field of Classification Search
CPC ............................. H04L 65/80; H04M 13/03
See application file for complete search history.

(56) References Cited

U.S. PATENT DOCUMENTS

| 6,175,871 | B1* | 1/2001 | Schuster | H04Q 11/0478 370/252 |
| 2006/0279437 | A1* | 12/2006 | Luby | H03M 13/1515 341/50 |
| 2006/0290808 | A1* | 12/2006 | Choi | H04N 21/431 348/468 |
| 2007/0079222 | A1* | 4/2007 | Kure | H04L 1/1877 714/776 |
| 2007/0101379 | A1* | 5/2007 | Pereira | H04N 21/2404 725/90 |

(Continued)

FOREIGN PATENT DOCUMENTS

JP    2007-311924 A    11/2007

*Primary Examiner* — Joseph Ustaris
*Assistant Examiner* — Rebecca Volentine
(74) *Attorney, Agent, or Firm* — Chip Law Group

(57) ABSTRACT

There is provided a transmission apparatus including a video signal transmission unit configured to transmit a video signal to another apparatus, a time information reception unit configured to receive, from the other apparatus, time information including a duration from reception of the video signal until a timing at which display of each frame in the video signal starts at the other apparatus, and a degree-of-redundancy determination unit configured to determine a degree of redundancy for the video signal transmitted from the video signal transmission unit based on the time information received by the time information reception unit.

11 Claims, 11 Drawing Sheets

(56) References Cited

U.S. PATENT DOCUMENTS

| | | | |
|---|---|---|---|
| 2007/0165524 A1* | 7/2007 | Mascolo | H04L 69/163 370/230 |
| 2007/0177719 A1* | 8/2007 | Dei | H04L 1/0041 380/28 |
| 2007/0201500 A1* | 8/2007 | Deshpande | H04L 47/10 370/412 |
| 2007/0204196 A1* | 8/2007 | Watson | H04L 1/1607 714/751 |
| 2008/0049846 A1* | 2/2008 | Nagafuji | H04N 21/4305 375/240.28 |
| 2010/0011274 A1* | 1/2010 | Stockhammer | H04L 1/0041 714/752 |
| 2011/0243217 A1* | 10/2011 | Sanjeewa | H04N 21/2404 375/240.01 |
| 2011/0252287 A1* | 10/2011 | Kure | H04N 19/63 714/758 |
| 2012/0039194 A1* | 2/2012 | Kure | H04N 19/30 370/252 |

* cited by examiner

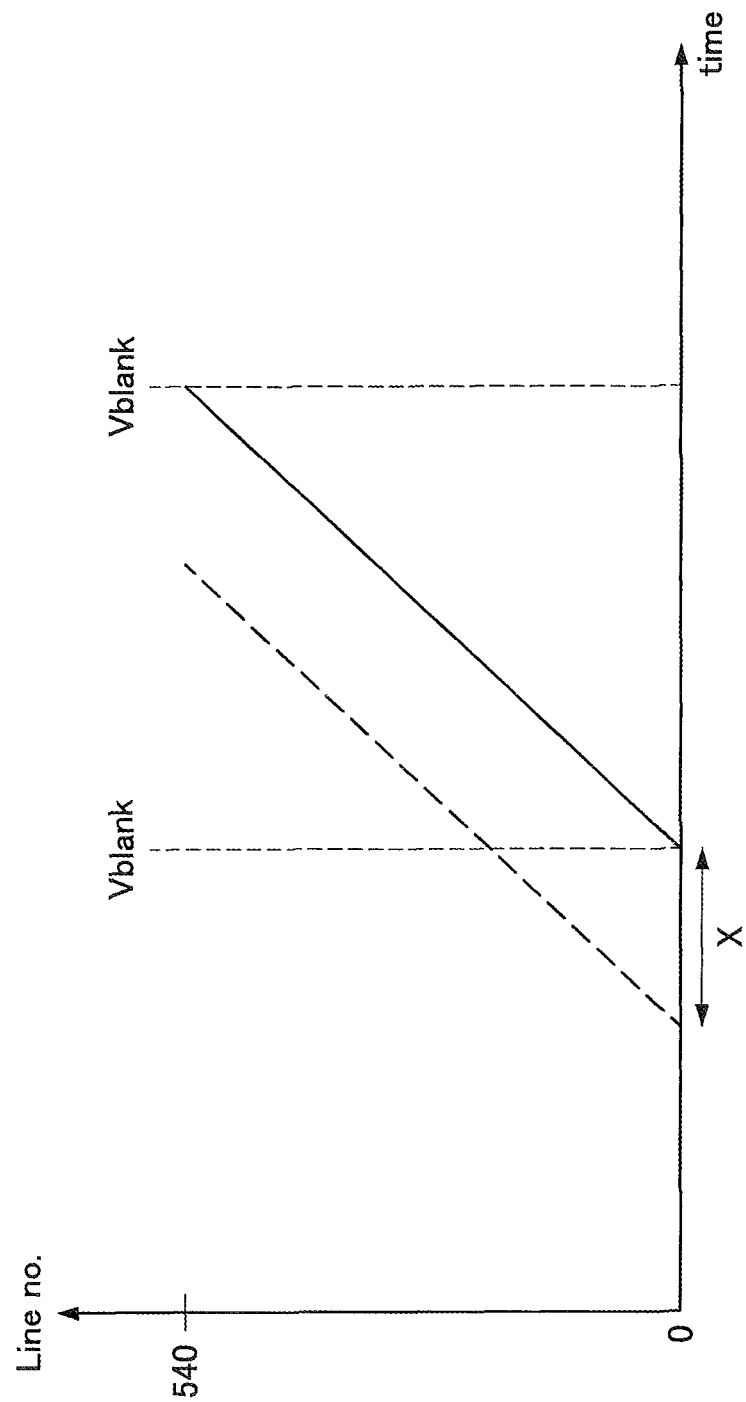

TRANSMISSION APPARATUS, TRANSMISSION METHOD, RECEPTION APPARATUS, RECEPTION METHOD, AND COMPUTER PROGRAM

CROSS REFERENCE TO RELATED APPLICATIONS

This application claims the benefit of Japanese Priority Patent Application JP 2012-241528 filed Nov. 1, 2012, the entire content of which is incorporated herein by reference.

BACKGROUND

The present disclosure relates to a transmission apparatus, a transmission method, a reception apparatus, a reception method, and a computer program.

Recently, there has been an increase in the demand for transmission of multimedia data including video data and audio data, for example, with low delay via the Internet or some other transmission path. An example of such an application is so-called remote surgery, in which two medical treatment locations that are far away from each other are connected via the Internet or the like, moving images of the surgical scene are transmitted from the operating room at one of the locations, and a surgeon operates a surgical instrument in that remote operating room while viewing the images at his/her own location. In this remote surgery application, it is desirable for the moving images to be transmitted with a delay interval of no more than a few frames.

In view of such demands, for example, JP-A-2007-311924 proposes a compression method based on wavelet conversion that compresses each few lines in each picture of the moving images as one compressed and encoded block. In this method, compression and FEC processing can be started without waiting until all of the data in a picture has been input. Further, even when transmitting the compressed data over a network and displaying the data at the reception side, the decoding processing can be started before receiving all the data in a picture. Therefore, as long as the network propagation delay is sufficiently small, the technology disclosed in JP-A-2007-311924 enables moving images to be transmitted in real time with a delay interval of no more than a few frames.

SUMMARY

Thus, in a multimedia data transmission system that is subject to very strict delay limits from the transmission side to the reception side, or for which such delays are prescribed, if the transmission side and the reception side are not in synchronization, that synchronization deviation causes the time until display to periodically fluctuate. Although there are some existing systems that issue a request from the reception side to the transmission side for the data to be retransmitted in order to improve the reliability of data transmission, if the time until display periodically fluctuates due to synchronization deviation, the likelihood of being able to recover the loss by retransmission also periodically fluctuates. Further, in order to recover the loss at the reception side, redundant packets are also added during the transmission from the transmission side to the reception side.

However, in existing systems, when adding redundant packets, there is no consideration given to periodic fluctuations such as those caused by synchronization deviation, so that in some cases more network bandwidth than necessary is used.

According to an embodiment of the present disclosure, there are provided a novel and improved transmission apparatus, transmission method, reception apparatus, reception method, and computer program, that are capable of increasing the recovery performance from synchronization deviation while suppressing network bandwidth usage when synchronization deviation has occurred in a transmission system for which low delay is demanded.

According to an embodiment of the present disclosure, there is provided a transmission apparatus including a video signal transmission unit configured to transmit a video signal to another apparatus, a time information reception unit configured to receive, from the other apparatus, time information including a duration from reception of the video signal until a timing at which display of each frame in the video signal starts at the other apparatus, and a degree-of-redundancy determination unit configured to determine a degree of redundancy for the video signal transmitted from the video signal transmission unit based on the time information received by the time information reception unit.

According to an embodiment of the present disclosure, there is provided a transmission method including transmitting a video signal to another apparatus, receiving, from the other apparatus, time information including a duration from reception of the video signal until a timing at which display of each frame in the video signal starts at the other apparatus, and determining a degree of redundancy for the transmitted video signal based on the received time information.

According to an embodiment of the present disclosure, there is provided a computer program that makes a computer execute transmission of a video signal to another apparatus, reception from the other apparatus of time information including a duration from reception of the video signal until a timing at which display of each frame in the video signal starts at the other apparatus, and determination of a degree of redundancy for the transmitted video signal based on the received time information.

According to an embodiment of the present disclosure, there is provided a reception apparatus including a video signal reception unit configured to receive a video signal from another apparatus, a time measurement unit configured to measure a duration from reception of the video signal by the video signal reception unit until a timing at which display of each frame in the video signal starts, and a time information transmission unit configured to transmit, to the other apparatus, time information including information about the duration measured by the time measurement unit.

According to an embodiment of the present disclosure, there is provided a reception method including receiving a video signal from another apparatus, measuring a duration from reception of the video signal until a timing at which display of each frame in the video signal starts, and transmitting, to the other apparatus, time information including information about the measured duration.

According to an embodiment of the present disclosure, there is provided a computer program that makes a computer execute reception of a video signal from another apparatus, measurement of a duration from reception of the video signal until a timing at which display of each frame in the video signal starts, and transmission to the other apparatus of time information including information about the measured duration.

According to one or more of embodiments of the present disclosure, provided are a novel and improved transmission apparatus, transmission method, reception apparatus, reception method, and computer program, that are capable of increasing the recovery performance from synchronization deviation while suppressing network bandwidth usage when synchronization deviation has occurred in a transmission system for which low delay is demanded.

BRIEF DESCRIPTION OF THE DRAWINGS

FIG. 11 is an explanatory diagram illustrating an example of capture and display timing of moving images.

DETAILED DESCRIPTION OF THE EMBODIMENT(S)

Figure 1:
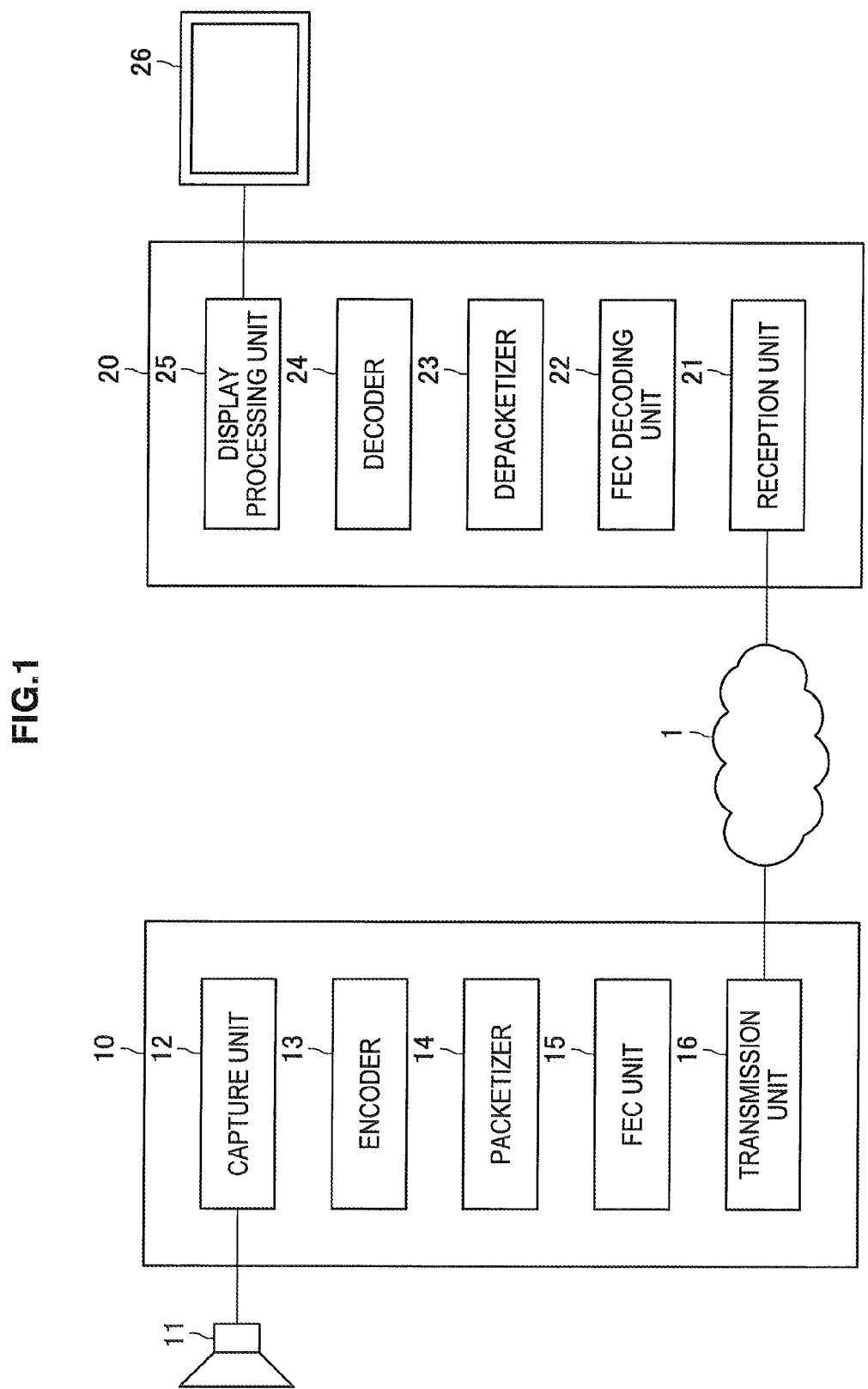
FIG. 1 is an explanatory diagram illustrating a configuration example of an existing compression transmission system for compressing and transmitting multimedia data.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will now be made in the following order.
<1. Outline of the existing technology>
<2. An embodiment of the present disclosure>
(Envisaged network system)
(Function configuration example)
(Communication system operation example)
<3. Summary>
<1. Outline of the Existing Technology>

Before describing a preferred embodiment of the present disclosure in detail, first an outline of the existing technology will be described with reference to the drawings. After the description of an outline of the existing technology, a preferred embodiment of the present disclosure will be described in detail.

The RTP (real-time transport protocol) is defined by IETF RFC3550 as an Internet technology suitable for streaming transmission methods. With data transfer based on RTP, a time stamp is added to the packets as time information. By grasping the temporal relationship between the transmission side and the reception side based on this time stamp, reproduction can be carried out in synchronization without being affected by delay variation (jitter) of packet transfer.

However, RTP does not guarantee data transfer during actual time. Similar to other packets, RTP packets can also be lost or subjected to delayed delivery because factors such as packet delivery priority, settings, and management are not within the scope of the transport service provided by RTP. Even if such delayed delivery or packet loss does occur, the reception side can reproduce the data by utilizing just the packets that have arrived within the expected time. This is because a certain level of reproduction is possible even if the some of the video images or audio data has been lost.

It is noted that packets whose delivery was delayed or for which an error occurred are discarded as is at the reception side. Namely, there is also the problem that even if high-quality data is sent the data may not be able to be properly reproduced due to packet loss and errors. Especially, since it is said that $10^{-5}$ errors occur over a wired section and $10^{-3}$ or more errors occur over a wireless section, from the perspective of maintaining the quality of the delivered media, reliability is low if RTP is utilized as is.

In view of this, there is a streaming transmission method in which a retransmission request is issued and packets are retransmitted based on TCP, which has a high data transmission reliability. However, although TCP is effective against errors, throughput is low and there are many delays, so that even if packets are retransmitted they may not arrive in time for reproduction.

Accordingly, examples of methods for improving the reliability of data transmission using RTP include automatic retransmission, i.e., an ARQ (Auto Repeat reQuest) method, and a forward error correction encoding method, i.e., a FEC (forward error correction) method.

The ARQ method is a method that uses the sequence number of the RTP packets to detect the packets that have been lost, and issues a request from the reception terminal to the transmission terminal for the lost packets to be retransmitted. Further, the FEC method is a method that performs redundant encoding using error correction encoding, such as Reed-Solomon (RS) encoding, using a plurality of packets as one FEC block. For example, when using (n,k) RS encoding, if there are k number of original packets, n-k redundant packets can be generated (wherein n>k). In this case, by transmitting a total of n packets from the transmission apparatus, if the reception apparatus receives k number of packets among the n packets, the reception apparatus can regenerate k number of original packets based on RS decoding processing.

Accordingly, an outline of the existing technology when the FEC method is used in a streaming transmission method will be described below.

FIG. 1 is an explanatory diagram illustrating a configuration example of an existing compression transmission system for compressing and transmitting multimedia data. The compression transmission system illustrated in FIG. 1 includes a transmission apparatus 10 and a reception apparatus 20. The transmission apparatus 10 and the reception apparatus 20 are each connected to a network 1, and can communicate with each other via the network 1.

The transmission apparatus 10 is configured from a capture unit 12 that captures images taken by an imaging apparatus 11, an encoder 13 that encodes the images captured by the capture unit 12, a packetizer 14 that converts data encoded by the encoder 13 into packets, a FEC unit 15 that performs FEC (forward error correction) processing, and a transmission unit 16 that transmits data to the reception apparatus 20.

The reception apparatus 20 is configured from a reception unit 21 that receives data transmitted from the transmission apparatus 10 via the network 1, a FEC decoding unit 22 that decodes data encoded by forward error correction processing, a depacketizer 23 that depacketizes data decoded by the FEC decoding unit 22, a decoder 24 that decodes depacketized data, and a display processing unit 25 that outputs data decoded by the decoder 24 to a display 26.

Figure 2:
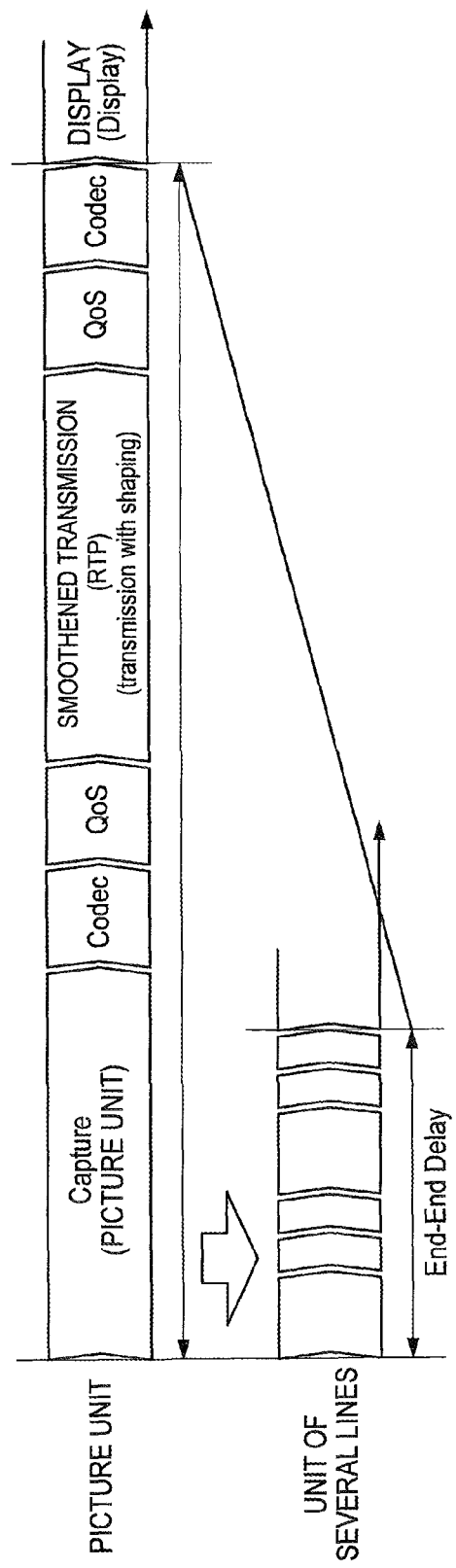
FIG. 2 is an explanatory diagram illustrating a concept of the processing performed by a compression transmission system.

For ordinary compression transmission, the compression transmission system illustrated in FIG. 1 performs a series of processes (image capture, encoding/decoding, FEC processing, and display processing) with the transmission apparatus 10 and the reception apparatus 20 in picture units (fields, frames). Further, the compression transmission system illustrated in FIG. 1 can realize low-delay transmission by dividing one picture into line blocks formed from several lines, and performing these processes in parallel. FIG. 2 is an explanatory diagram illustrating a concept of the processing performed by the compression transmission system illustrated in FIG. 1.

Figure 3:
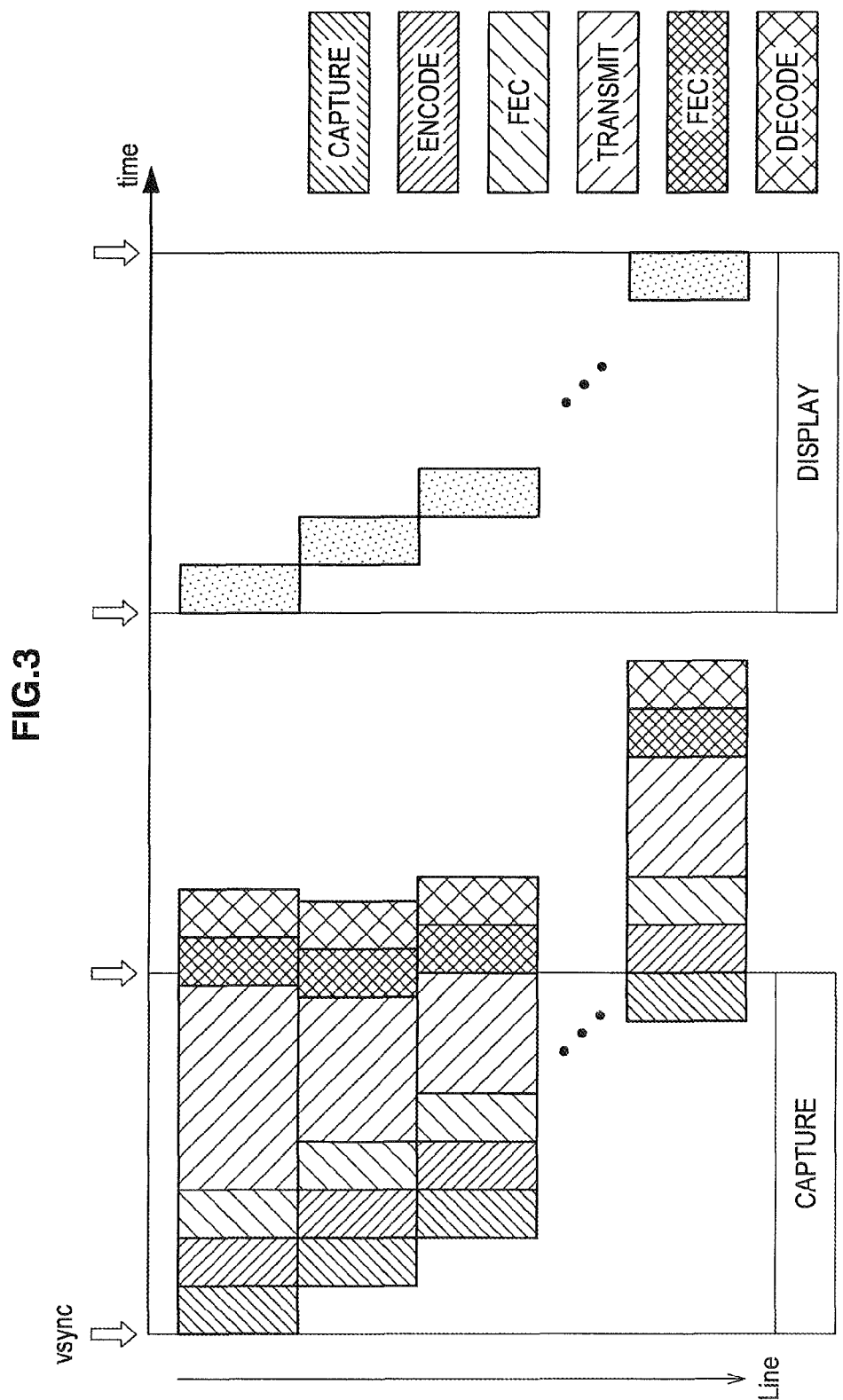
FIG. 3 is an explanatory diagram illustrating a concept of the processing performed by a compression transmission system.

In addition, when performing processing in line block units, the transmission apparatus 10 executes pipelined processing. FIG. 3 is an explanatory diagram illustrating a concept of the processing performed by the compression transmission system illustrated in FIG. 1. In FIG. 3, a state is illustrated in which the transmission apparatus 10 and the reception apparatus 20 are in synchronization. When compressing and transmitting multimedia data from the transmission apparatus 10 to the reception apparatus 20, the reception apparatus 20 executes display processing based on the timing at which a vsync (vertical synchronization signal) is transmitted.

An outline of the existing technology was described above. Such a system enables low-delay transmission if the transmission apparatus 10 and the reception apparatus 20 are in synchronization. However, the transmission apparatus 10 and the reception apparatus 20 can fall out of synchronization for various reasons. As described above, if the transmission side and the reception side are not in synchronization, the time until display periodically fluctuates due to that deviation in synchronization. Although some existing systems are configured to issue a request from the reception side to the transmission side for retransmission of the data in order to improve data transmission reliability, if the time until display periodically fluctuates due to synchronization deviation, the likelihood of being able to recover the loss by retransmission also periodically fluctuates.

However, as described above, with an existing system, during addition of redundant packets, no consideration is given to periodic fluctuations such as those caused by synchronization deviation. Consequently, in some cases more network bandwidth is used than is necessary.

Accordingly, in the below-described embodiment of the present disclosure, a technology will be described that, when synchronization deviation has occurred in a transmission system for which low delay is demanded, enables the recovery performance from synchronization deviation to be increased while suppressing network bandwidth usage.
<2. Embodiment of the Present Disclosure>
(Envisaged Network System)

First, the network system that is envisaged according to an embodiment of the present disclosure will be described. The network system that is envisaged according to an embodiment of the present disclosure is a transmission system that captures and compresses packets on the transmission side, generates redundant packets for recovery when packets are lost on the network, and transmits the generated redundant packets with the data packets. In this transmission system, the reception side receives the packets from the transmission side, and if a packet has been lost, recovers using a redundant packet. If recovery is not possible even using the redundant packets, the reception side issues a request to the transmission side for retransmission.

Here, the reception side can recover the loss if the retransmitted packet arrives from the transmission side in time for the display start illustrated in FIG. 3. If the retransmitted packet does not arrive in time for the display start, the reception side transfers the received data as is to the decoder, and displays the data according to the display timing. It is noted that in the present embodiment, decoded data is defined as "display-ready" data. The reception side does not display or write to the buffer for display until the display timing is reached even if the data is display-ready.

In addition, the envisaged network system according to an embodiment of the present disclosure is subject to the following restrictions.
1. The system processes in units no greater than frame units (referred to here as "line block units").
2. The time taken by the system from capture to display is no greater than one frame or is a comparatively fixed value that acts like it is no greater than one frame. Namely, the delay at the reception side does not extend across frames.
3. A state exists in which the transmission side and the reception side are not in synchronization.

A technology will now be described that, in such a network system in which low-delay is demanded, enables the recovery performance from synchronization deviation to be increased while suppressing network bandwidth usage when synchronization deviation has occurred.
(Function Configuration Example)

Figure 4:
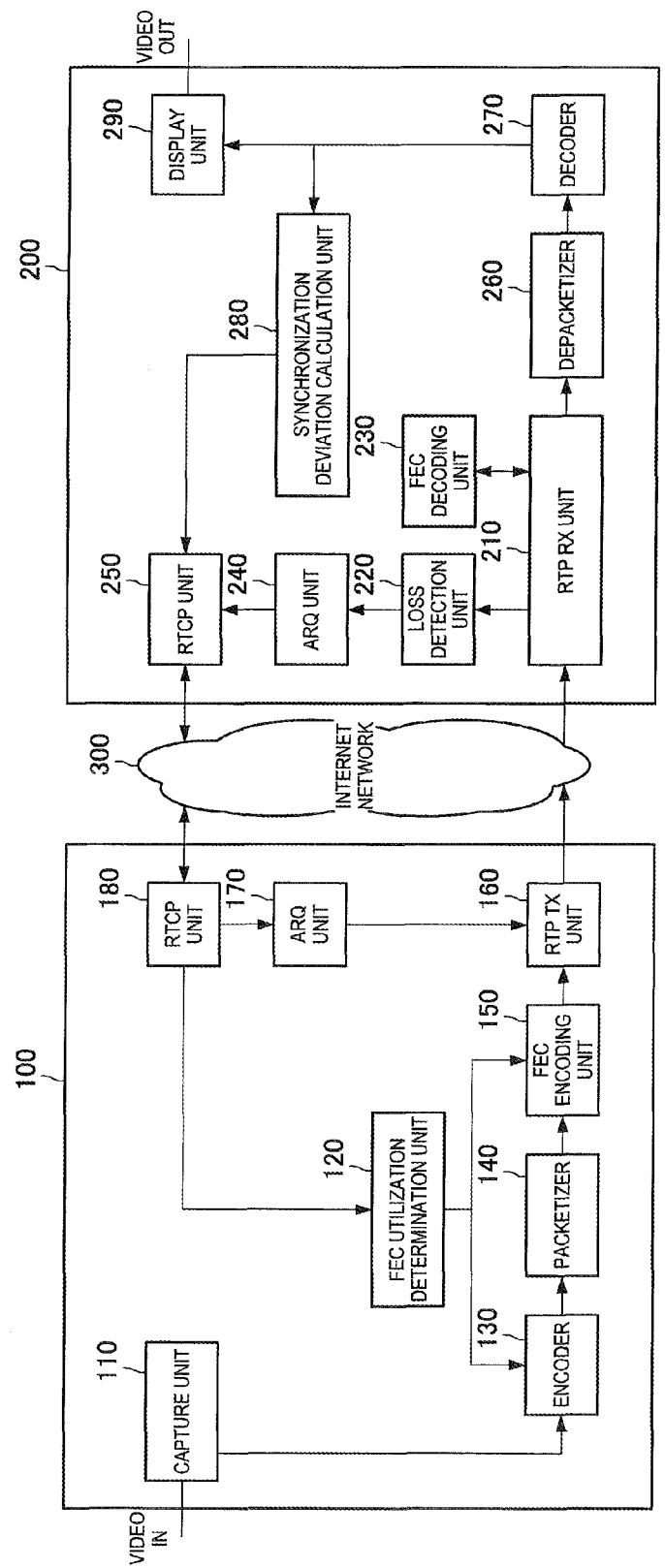
FIG. 4 is an explanatory diagram illustrating a function configuration example of a communication system according to an embodiment of the present disclosure.

FIG. 4 is an explanatory diagram illustrating a function configuration example of a communication system according to an embodiment of the present disclosure. A function configuration example of the communication system according to an embodiment of the present disclosure will be described below with reference to FIG. 4.

As illustrated in FIG. 4, the communication system according to an embodiment of the present disclosure is configured from a transmission apparatus 100 and a reception apparatus 200. The transmission apparatus 100 and the reception apparatus 200 are connected to an Internet network 300, and can communicate with each other via the Internet network 300.

The transmission apparatus 100 is configured from a capture unit 110, a FEC utilization determination unit 120, an encoder 130, a packetizer 140, a FEC encoding unit 150, a RTP TX unit 160, an ARQ unit 170, and a RTCP unit 180.

Further, the reception apparatus 200 is configured from an RTP RX unit 210, a loss detection unit 220, a FEC decoding unit 230, an ARQ unit 240, a RTCP unit 250, a depacketizer 260, a decoder 270, a synchronization deviation calculation unit 280, and a display unit 290.

First, each unit in the transmission apparatus 100 will be described. The capture unit 110 captures a video signal that is transmitted to the transmission apparatus 100 in line block units. The video signal transmitted to the transmission apparatus 100 is generated by, for example, a video camera or some other imaging apparatus. When a video signal has been captured in line block units, the capture unit 110 transmits the captured signal to the encoder 130.

The encoder 130 encodes the signal in line block units captured by the capture unit 110 based on a predetermined method. For example, the encoder 130 may encode the signal in line block units based on a method like that discussed in JP-A-2007-311924, in which each few lines in each picture of the moving images are compressed based on wavelet conversion as one compressed and encoded block. However, the encoding method according to an embodiment of the present disclosure is not limited to this example. The encoder 130 can encode the signal in line block units based on any encoding method, as long as that encoding method can be applied in the above-described envisaged network system. The encoder 130 transmits the encoded data to the packetizer 140. Further, if it is determined to execute FEC processing with the FEC utilization determination unit 120, the encoder 130 executes processing based on that determination.

The packetizer 140 converts the data encoded by the encoder 130 into RTP packets. Then, the packetizer 140 transmits the generated RTP packets to the FEC encoding unit 150.

The FEC encoding unit 150 subjects the RTP packets generated by the packetizer 140 to FEC encoding. Here, if it was determined by the FEC utilization determination unit 120 to perform FEC encoding, the FEC encoding unit 150 performs redundant encoding of the original data based on a determined degree of redundancy. After the FEC encoding unit 150 has subjected the RTP packets generated by the packetizer 140 to FEC encoding, the FEC encoding unit 150 transmits the encoded data to the RTP TX unit 160. The FEC encoding unit 150 performs, as the FEC redundant encoding, redundant encoding using an erasure error correction code such as a Reed-Solomon code, for example. In the present embodiment, a pair formed from the number of original data packets and the number of redundant packets is handled as one redundant code unit, i.e., a FEC block.

The RTP TX unit 160 transmits the data encoded by the FEC encoding unit 150 toward the reception apparatus 200. Further, if a retransmission control has been performed by the below-described ARQ unit 170, the RTP TX unit 160 transmits the packet to be retransmitted toward the reception apparatus 200.

The ARQ unit 170 performs retransmission control based on an ARQ method (Automatic Repeat reQuest; error detection automatic retransmission request method). The RTCP unit 180 receives a NACK packet from the reception apparatus 200. The NACK packet is a packet transmitted from the reception apparatus 200 in order to request retransmission of a lost packet.

Next, each unit in the reception apparatus 200 will be described. The RTP RX unit 210 receives the data transmitted from the transmission apparatus 100. When the RTP RX unit 210 receives the data transmitted from the transmission apparatus 100, the RTP RX unit 210 transmits the received data to the loss detection unit 220, the FEC decoding unit 230, and the depacketizer 260.

The loss detection unit 220 detects whether there are any missing packets in the data received by the RTP RX unit 210. For example, the loss detection unit 220 scans the sequence numbers described in the RTP packet header, and if the sequence numbers of the received RTP packets are not consecutive, determines that a packet has been lost. If there is a missing packet in the data received by the RTP RX unit 210, the loss detection unit 220 instructs the ARQ unit 240 to add the lost data to a retransmission request list (NACK list).

The FEC decoding unit 230 performs decoding processing based on the FEC method using the data received by the RTP RX unit 210. The data subjected to decoding processing based on the FEC method by the FEC decoding unit 230 is returned to the RTP RX unit 210, and then transmitted to the depacketizer 260.

The ARQ unit 240 generates a retransmission request list (NACK list) concerning the data detected by the loss detection unit 220 to be missing. After the NACK list has been generated, the ARQ unit 240 reads the NACK packet information from that NACK list at a designated timing, and transmits the read NACK packet information to the RTCP unit 250.

Two times are set in the NACK list for each piece of NACK packet information, a "NACK timeout" and a "NACK deadline". The ARQ unit 240 of the reception apparatus 200 transmits the NACK packet after a packet loss is initially detected. If the retransmitted packet is not received by "NACK timeout", which is the point at which the elapsed time since transmission of the NACK packet has passed a predetermined duration, the ARQ unit 240 repeats the step of retransmitting the NACK packet until the "NACK deadline" is reached. The NACK timeout is usually set at a point after a RTT time (Round Trip Time; round trip delay time) since transmission of the NACK packet has passed. The "NACK deadline" is set a RTT duration before the packet arrival deadline, such as the expected reproduction time of that packet data.

The RTCP unit 250 transmits the NACK packet to the transmission apparatus 100 based on the NACK packet information transmitted from the ARQ unit 240.

It is noted that as the NACK packet format, the RTCP NACK packet described in the IETF Internet Draft "Extended RTP Profile for RTCP-based Feedback", for example, may be used.

The depacketizer 260 executes processing for reconfiguring the RTP packet data into compressed image data. When the RTP packet data has been reconfigured into compressed image data, the depacketizer 260 transmits the compressed image data to the decoder 270.

The decoder 270 executes processing for decoding the compressed image data transmitted from the depacketizer 260. When the compressed image data has been decoded, the decoder 270 transmits the decoded data to the synchronization deviation calculation unit 280 and the display unit 290.

The synchronization deviation calculation unit 280 calculates synchronization deviation based on the packet reception timing. Although the processing for calculating synchronization deviation by the synchronization deviation calculation unit 280 will be described below, briefly stated, the synchronization deviation calculation unit 280 calculates the duration from the arrival of the start of a picture until display for each picture, and then calculates the time moving average of that duration. Further, the synchronization deviation calculation unit 280 provides feedback to the transmission apparatus 100 of when that time moving average is at a maximum and at a minimum. By calculating synchronization deviation with the synchronization deviation calculation unit 280 and providing feedback to the transmission apparatus 100, when synchronization deviation has occurred, the recovery performance from synchronization deviation can be increased while suppressing network bandwidth usage.

It is noted that in the present exemplary embodiment, a state in which the vertical blanking interval (Vblank) timing at the transmission apparatus 100 and the reception apparatus 200 matches is referred to as "in synchronization", and a state in which the vertical blanking interval (Vblank) timing at the transmission apparatus 100 and the reception apparatus 200 does not match is referred to as "synchronization deviation is occurring".

The display unit 290 executes display processing of the data decoded by the decoder 270. For example, the display unit 290 outputs the data decoded by the decoder 270 to a video display apparatus, such as a display etc., via a video output OF (video out).

It is noted that the transmission apparatus 100 and the reception apparatus 200 illustrated in FIG. 4 can perform all of the processing in line block units.

A function configuration example of a communication system according to an embodiment of the present disclosure was described above with reference to FIG. 4. Next, an operation example of a communication system according to an embodiment of the present disclosure will be described.

(Communication System Operation Example)

Figure 5:
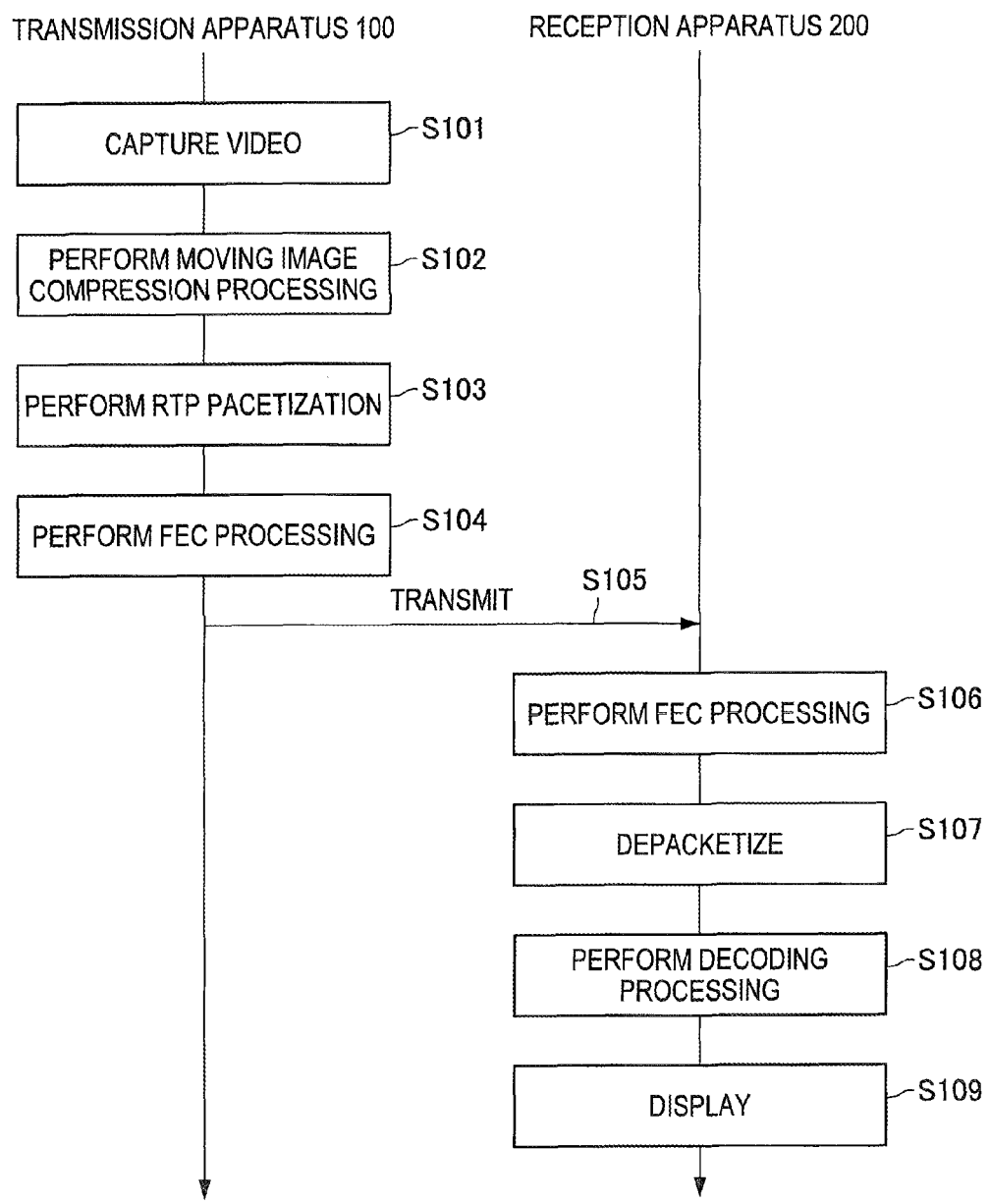
FIG. 5 is a flow diagram illustrating an operation example of a communication system according to an embodiment of the present disclosure.

First, the transmission processing that is performed between the transmission apparatus 100 and the reception apparatus 200 during normal periods will be described. FIG. 5 is a flow diagram illustrating an operation example of a communication system according to an embodiment of the present disclosure. The flow diagram illustrated in FIG. 5 illustrates an operation example of transmission processing performed during normal periods between the transmission apparatus 100 and the reception apparatus 200. An operation example of a communication system according to an embodiment of the present disclosure will now be described with reference to FIG. 5.

In the transmission apparatus 100, first, the capture unit 110 captures in line blocks video data input from a video input IF (video IN) via a video camera, for example (step S101), and transmits the captured video data to the encoder 130 for performing moving image data compression processing. The encoder 130 executes moving image compression processing on the moving image data (step S102). The packetizer 140 then executes RTP packetization processing on the data subjected to moving image compression processing. Further, the FEC encoding unit 150 executes FEC processing on the data subjected to the RTP packetization processing (step S104), and the RTP TX unit 160 transmits the data subjected to FEC processing as RTP packets to the network (step S105).

In the reception apparatus 200, when the RTP RX unit 210 receives the RTP packets transmitted from the transmission apparatus 100 by the RTP TX unit 160, the FEC decoding unit 230 executes FEC processing (step S106). Then, the depacketizer 260 performs reconfiguration processing (depacketizing) on the compressed image data of the RTP packet data (step S107), and the decoder 270 performs decoding processing on the depacketized data (step S108). The display unit 290 then outputs the decoded video data to a video display apparatus, such as a display etc., via a video output I/F (video out) (step S109). Here, the display unit 290 outputs decoded video data to match the start timing of the vertical blanking interval.

By executing the series of processes like that illustrated in FIG. 5 with the transmission apparatus 100 and the reception apparatus 200, the moving images captured by the transmission apparatus 100 are output from the reception apparatus 200. Here, if the transmission apparatus 100 and the reception apparatus 200 are in synchronization, i.e., if the vertical blanking intervals of the transmission apparatus 100 and the reception apparatus 200 match, the number of redundant packets to be added in the FEC processing performed by the transmission apparatus 100 can be made constant.

Figure 6:
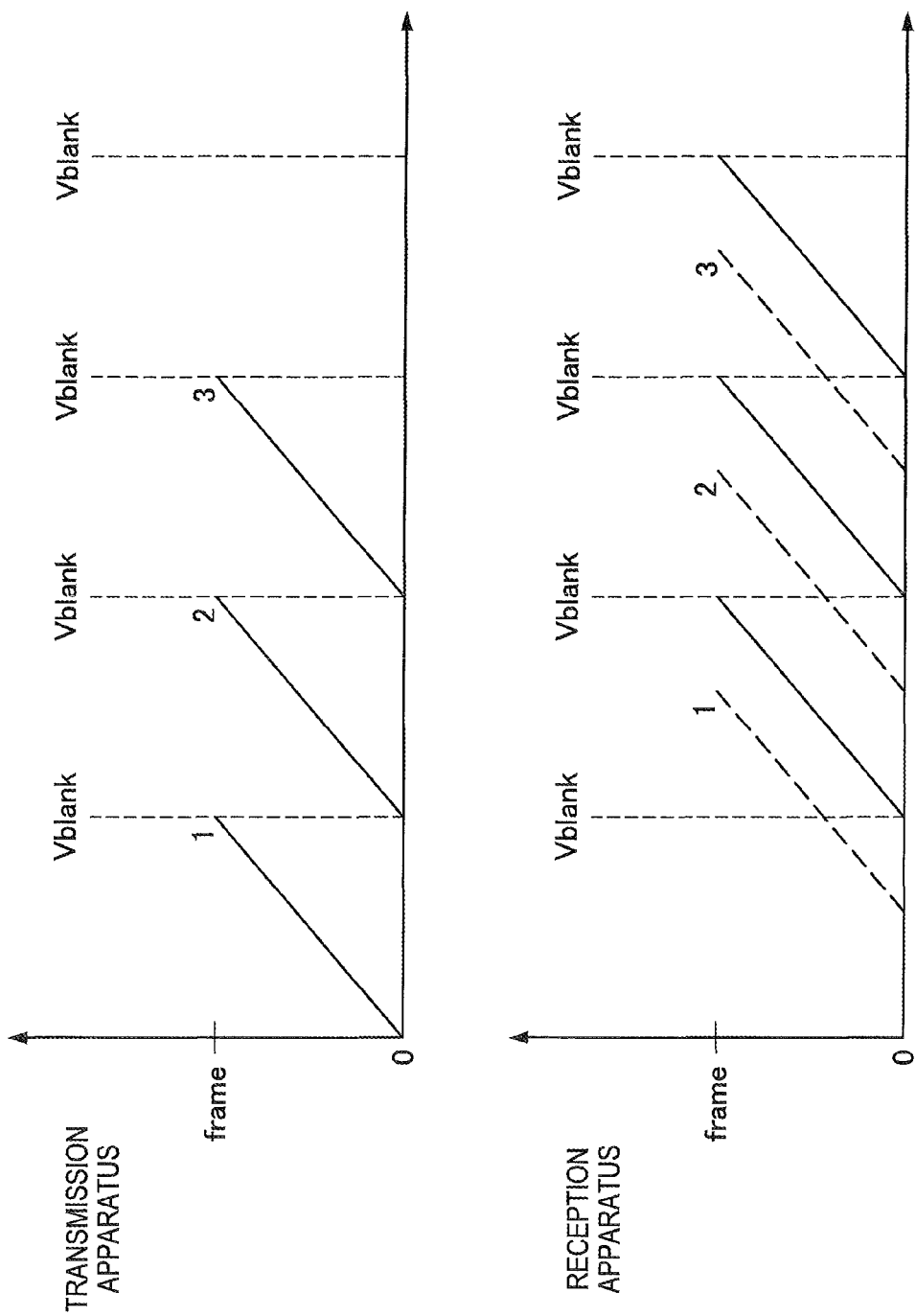
FIG. 6 is an explanatory diagram illustrating capture and display timing of moving images.

FIG. 6 is an explanatory diagram illustrating capture and display timing of moving images in a state in which the transmission apparatus 100 and the reception apparatus 200 are in synchronization. In the graph illustrated in FIG. 6, the horizontal axis represents time and the vertical axis represents a line, along which the word "frame" indicates the number of lines in one frame. The reception apparatus 200 outputs the data transmitted from the transmission apparatus 100 to match the timing of the signal Vblank that indicates the start timing of the vertical blanking interval.

As illustrated in FIG. 6, if the transmission apparatus 100 and the reception apparatus 200 are in synchronization, the interval between the timing at which the data received from the transmission apparatus 100 is ready to be displayed by the reception apparatus 200 and the timing at which the display is started by the reception apparatus 200 is constant. If this interval is constant, as described above, the number of redundant packets added in the FEC processing by the transmission apparatus 100 can be made constant. This is because if the interval between the display-ready state timing and the display-start timing is constant, it is easier to consider the duration until retransmission of packets that have been lost.

Namely, although the reception apparatus 200 performs error correction using redundant packets, in some cases it may not be possible to do so. In such a case, the reception apparatus 200 issues a request to the transmission apparatus 100 for retransmission. However, as illustrated in the above-described envisaged network, in order to prevent a delay that extends across frames from occurring, it is desirable that the addition of redundant packets takes the retransmission of packets into consideration. Therefore, if the interval between the display-ready state timing and the display-start timing is constant, this allows just the right number of redundant packets to be added, so that wasteful usage of network bandwidth can be avoided.

However, if the transmission apparatus 100 and the reception apparatus 200 are not in synchronization, the interval between the timing at which the data received from the transmission apparatus 100 is ready to be displayed by the reception apparatus 200 and the timing at which the display is started by the reception apparatus 200 is not constant. Specifically, if the transmission apparatus 100 and the reception apparatus 200 are not in synchronization, the interval between the display-ready timing and the display-start timing periodically changes.

Figure 7:
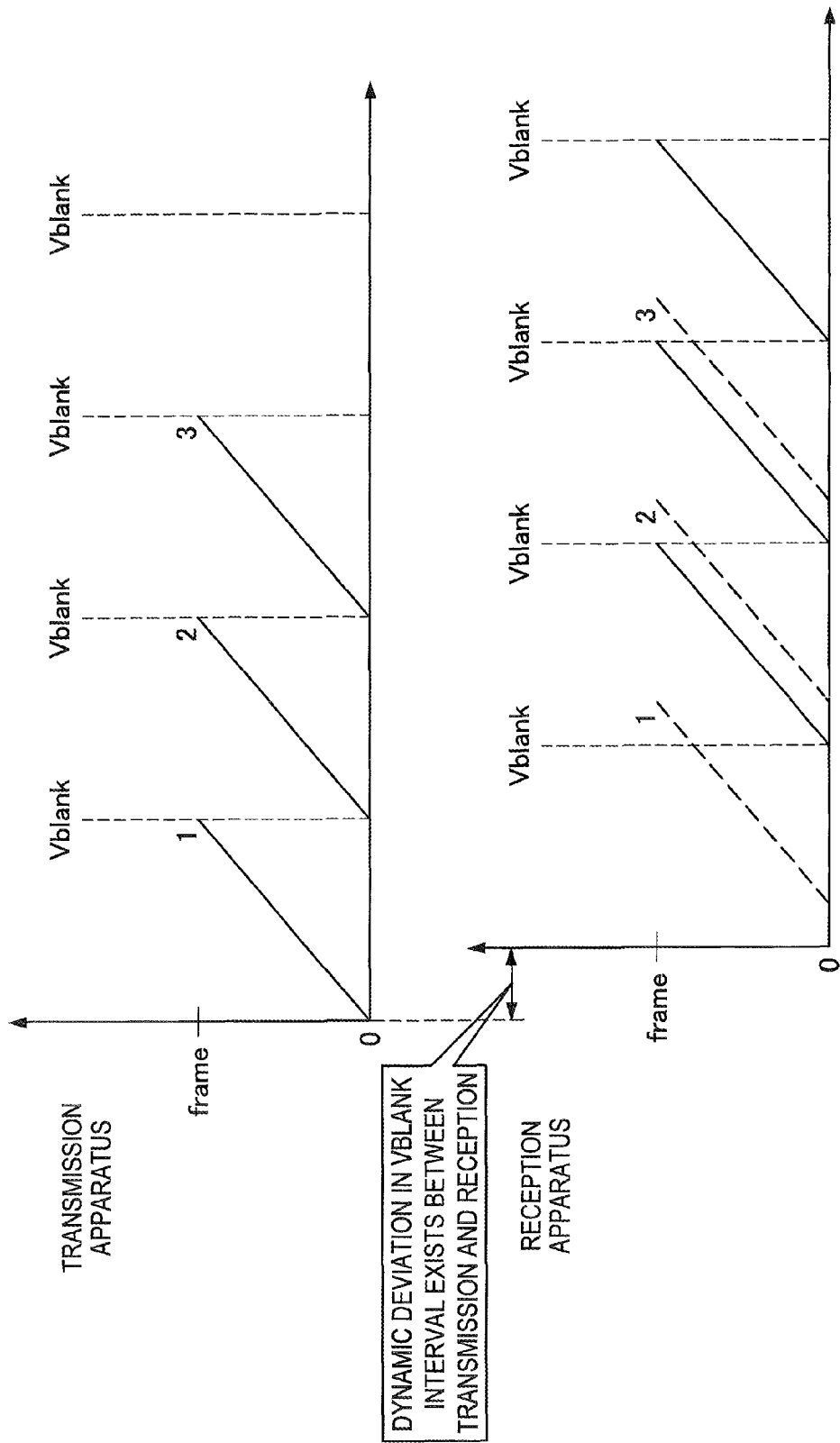
FIG. 7 is an explanatory diagram illustrating capture and display timing of moving images.

FIG. 7 is an explanatory diagram illustrating capture and display timing of moving images in a state in which the transmission apparatus 100 and the reception apparatus 200 are not in synchronization. Similar to FIG. 6, in the graph illustrated in FIG. 7, the horizontal axis represents time and the vertical axis represents a line, along which the word "frame" indicates the number of lines in one frame.

Thus, when the transmission apparatus 100 and the reception apparatus 200 are not in synchronization, the vertical blanking interval timing between the transmission apparatus 100 and the reception apparatus 200 does not match. Further, when the transmission apparatus 100 and the reception apparatus 200 are not in synchronization, the Vblank interval between the transmission apparatus 100 and the reception apparatus 200 periodically fluctuates. If the Vblank interval between the transmission apparatus 100 and the reception apparatus 200 periodically fluctuates, the interval between the timing at which the data received from the transmission apparatus 100 is ready to be displayed by the reception apparatus 200 and the timing at which the display is started by the reception apparatus 200 also periodically fluctuates.

Figure 8:
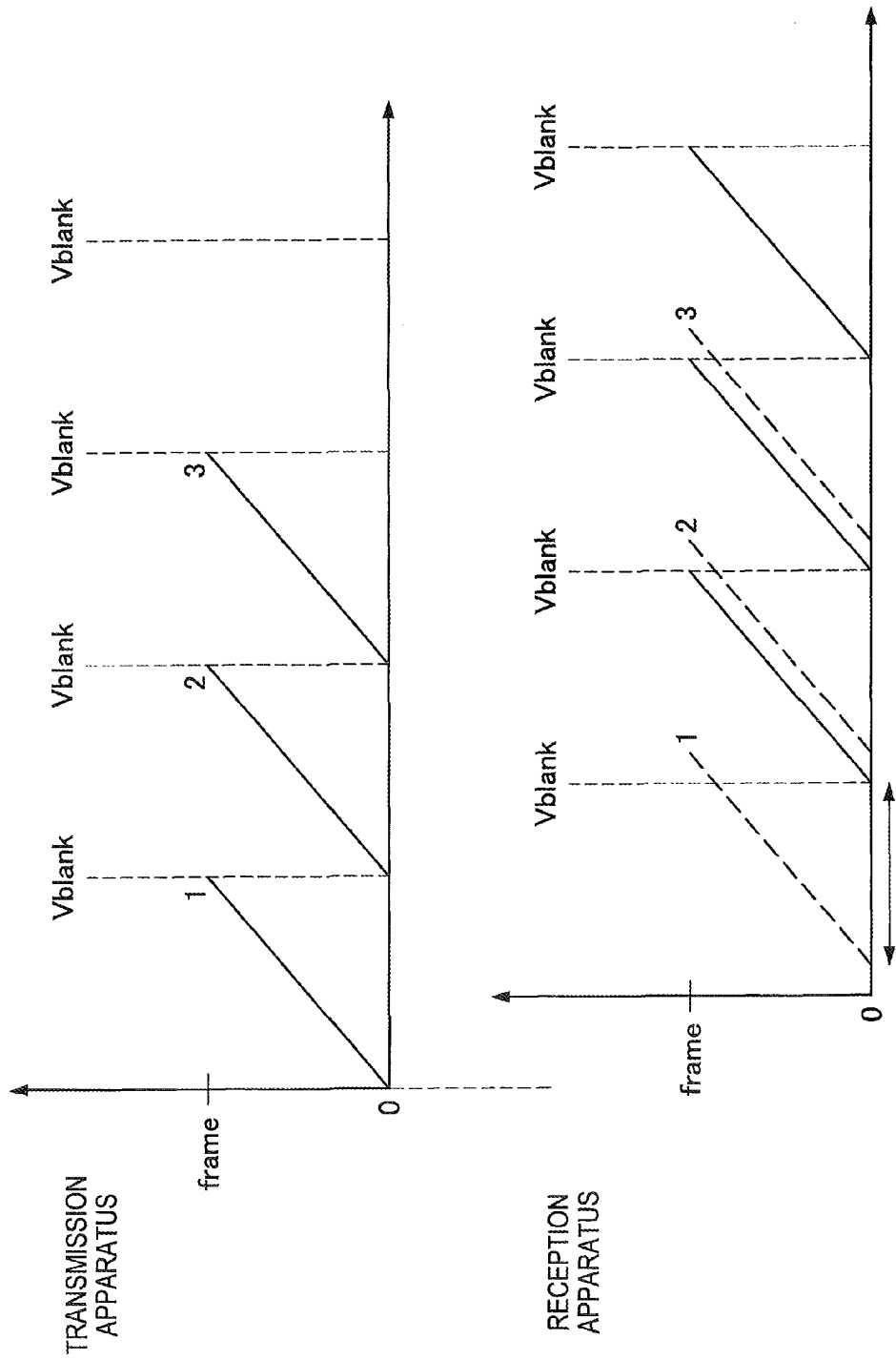
FIG. 8 is an explanatory diagram illustrating capture and display timing of moving images.
Figure 9:
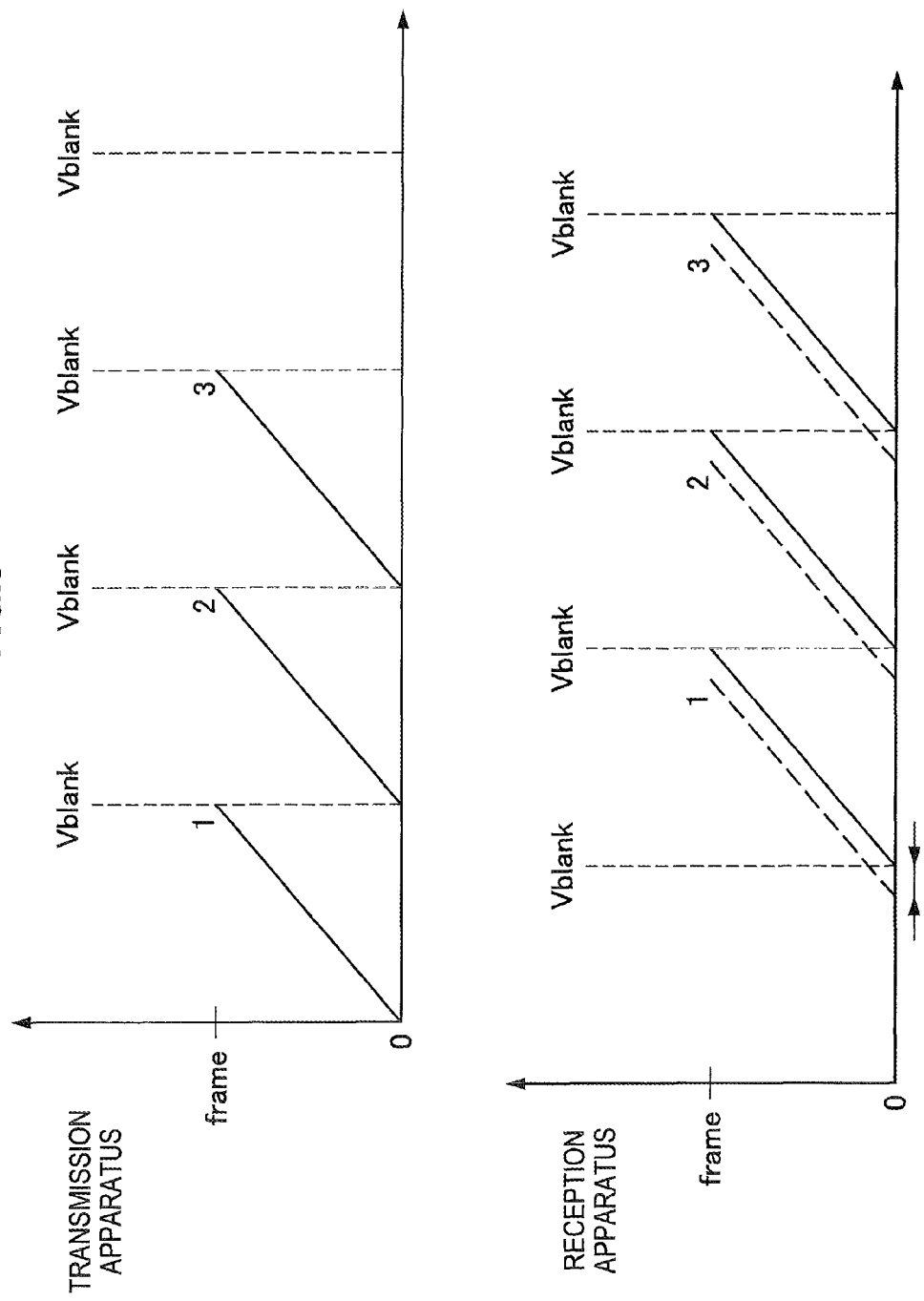
FIG. 9 is an explanatory diagram illustrating capture and display timing of moving images.

FIGS. 8 and 9 are explanatory diagrams illustrating capture and display timing of moving images in a state in which the transmission apparatus 100 and the reception apparatus 200 are not in synchronization. Similar to FIGS. 6 and 7, in the graphs illustrated in FIGS. 8 and 9, the horizontal axis represents time and the vertical axis represents a line, along which the word "frame" indicates the number of lines in one frame.

The graph in FIG. 8 illustrates an example of a case in which the interval between the timing at which the data received from the transmission apparatus 100 is ready to be displayed by the reception apparatus 200 and the timing at which the display is started by the reception apparatus 200 is at a maximum. The graph in FIG. 9 illustrates an example of a case in which the interval between the timing at which the data received from the transmission apparatus 100 is ready to be displayed by the reception apparatus 200 and the timing at which the display is started by the reception apparatus 200 is at a minimum.

Therefore, even when the transmission apparatus 100 and the reception apparatus 200 are not in synchronization, in order to prevent a delay that extends across frames from occurring, it is desirable that the addition of redundant packet takes the retransmission of packets into consideration. However, if the transmission apparatus 100 and the reception apparatus 200 are not in synchronization, as illustrated in FIGS. 8 and 9, the interval between the timing at which the data received from the transmission apparatus 100 is ready to be displayed by the reception apparatus 200 and the timing at which the display is started by the reception apparatus 200 periodically fluctuates. If the number of redundant packets added by the transmission apparatus 100 is constant, this fluctuation can result in the retransmission of the packets not being in time for the Vblank timing at the reception apparatus 200, or can result in too many redundant packets being added.

Accordingly, in the transmission system according to an embodiment of the present disclosure, the transmission apparatus 100 executes redundant packet addition processing that takes periodic fluctuations such as those described above into consideration. By designing so that the transmission apparatus 100 executes redundant packet addition processing that takes periodic fluctuations into consideration, the transmission system according to an embodiment of the present disclosure can increase recovery performance from packet loss while eliminating wasteful usage of network bandwidth.

Figure 10:
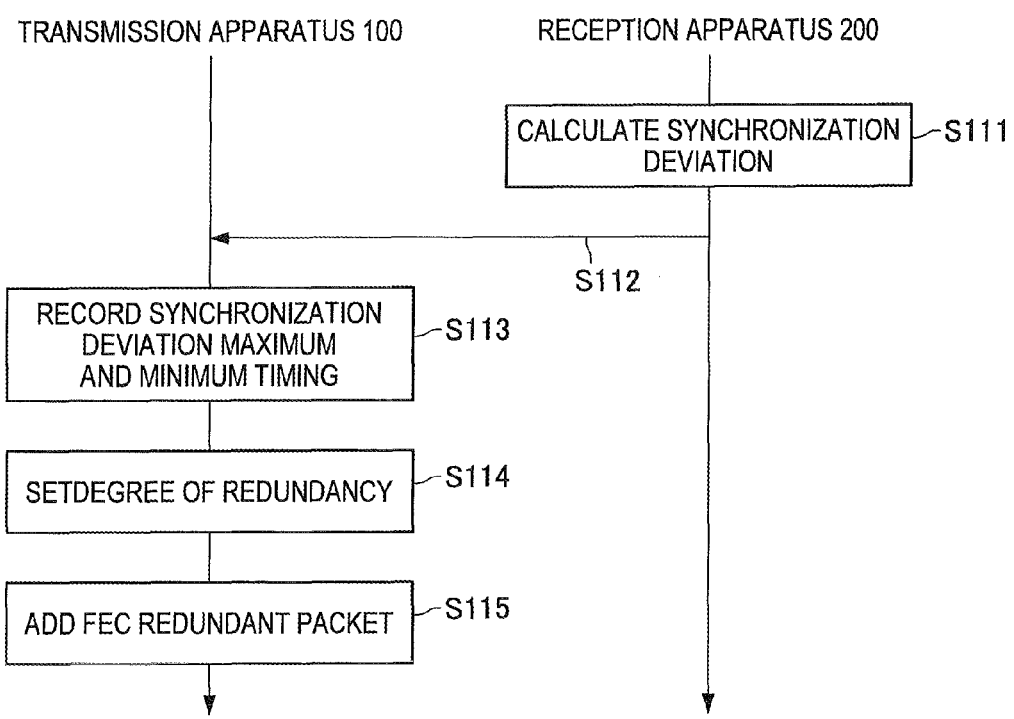
FIG. 10 is a flow diagram illustrating an operation example of a communication system according to an embodiment of the present disclosure.

FIG. 10 is a flow diagram illustrating an operation example of a communication system according to an embodiment of the present disclosure. The flow diagram illustrated in FIG. 10 illustrates an operation example when the transmission apparatus 100 and the reception apparatus 200 are not in synchronization. An operation example of a communication system according to an embodiment of the present disclosure will now be described with reference to FIG. 10.

In the reception apparatus 200, the synchronization deviation calculation unit 280 determines whether there is synchronization deviation between the transmission apparatus 100 and the reception apparatus 200, and if there is synchronization deviation, calculates that interval (step S111).

The synchronization deviation calculation unit 280 calculates synchronization deviation based on the reception timing of the packets. An example of that procedure will be described below. Further, the description of the calculation of synchronization deviation will also refer to FIG. 11. FIG. 11 is an explanatory diagram illustrating an example of capture and display timing of moving images by the reception apparatus 200.

The synchronization deviation calculation unit 280 collects statistical information about a duration X in FIG. 11 from when the start of a picture arrives, the video signal is decoded, and the decoded data is ready to be displayed until the data is displayed. Specifically, the synchronization deviation calculation unit 280 calculates the value of duration X for each picture. Then, the synchronization deviation calculation unit 280 calculates the time moving average Xavg of this X value. The time moving average Xavg of the X value is a periodically-fluctuating value that has a value between a minimum value of 0±a and a maximum value of Vblank Interval±b. It is noted that "Vblank Interval" corresponds to the interval of the Vblank signal.

It is noted that the minimum value of Xavg can be set so that it does not become zero. The minimum value of Xavg can be set so that it does not become zero by, for example, performing buffering in the reception apparatus 200 for a predetermined duration after the packets have been received from the transmission apparatus 100.

Further, at the point when Xavg is at the minimum value and at the point when Xavg is at the maximum value, the synchronization deviation calculation unit 280 sends a feedback message to the transmission apparatus 100 notifying the points at which that maximum value and minimum value occurred, and a difference D between the timing of the maximum value and the timing of minimum value (step S112). It is noted that the collection duration of the statistical information about the values of X by the synchronization deviation calculation unit 280 and the feedback interval to the transmission apparatus 100 can be arbitrarily set.

When the feedback message from the synchronization deviation calculation unit 280 is received by the RTCP unit 180, the transmission apparatus 100 records the timing of the minimum value (Tmin) and the timing of the maximum value (Tmax) of the Xavg calculated by the synchronization deviation calculation unit 280 with the FEC utilization determination unit 120 (step S113). The transmission apparatus 100 uses the timing of the minimum value (Tmin) and the timing of the maximum value (Tmax) of this synchronization deviation to determine a degree of redundancy with the FEC utilization determination unit 120 (step S114).

For example, at the timing (Tmin) at which Xavg is at the minimum value, since the time for given for the retransmission of the packets is at its shortest, the FEC utilization determination unit 120 determines the degree of redundancy so that just the maximum possible number of FEC redundant packets is added. On the other hand, at the timing (Tmax) at which Xavg is at the minimum value, since the time for given for the retransmission of the packets is at its longest, the FEC utilization determination unit 120 determines the degree of redundancy so that just the minimum possible number of FEC redundant packets is added.

It is noted that the maximum and the minimum possible number are values that change based on factors such as the performance of the transmission apparatus 100 and the reception apparatus 200, and the communication environment between the transmission apparatus 100 and the reception apparatus 200. Therefore, the maximum and the minimum possible number are values that change based on the circumstances, they are not fixed at a given value.

Further, when the degree of redundancy based on Xavg has been set by the FEC utilization determination unit 120, the FEC encoding unit 150 adds the FEC redundant packets based on the degree of redundancy set by the FEC utilization determination unit 120 (step S115).

Thus, by changing the degree of redundancy based on the value of Xavg sent as feedback from the reception apparatus 200, the number of FEC redundant packets transmitted from the transmission apparatus 100 to the reception apparatus 200 also changes. Therefore, the communication system according to an embodiment of the present disclosure can increase recovery performance from packet loss while eliminating wasteful usage of network bandwidth even when synchronization deviation has occurred between the transmission apparatus 100 and the reception apparatus 200.

Here, various methods may be employed as the method for setting the degree of redundancy by the FEC utilization determination unit 120. Examples of the method for setting the degree of redundancy by the FEC utilization determination unit 120 will be described below.

For example, the FEC utilization determination unit 120 can linearly change the degree of redundancy between the timing at which Xavg is at a minimum value and the timing at which Xavg is at a maximum value by setting a maximum value and a minimum value for the degree of redundancy.

Further, for example, the FEC utilization determination unit 120 can also use the RTT value when determining the degree of redundancy. The timing at which Xavg is at a minimum value and the timing at which Xavg is at a maximum value sent as feedback to the transmission apparatus 100 are also times that have some leeway for retransmission. Therefore, the FEC utilization determination unit 120 can also calculate the degree of redundancy to be used by using the average RTT of the timing at which Xavg is at a minimum value and the timing at which Xavg is at a maximum value and applying the techniques disclosed in JP-A-2011-119133, for example.

Obviously, the methods for setting the degree of redundancy with the FEC utilization determination unit 120 described here are just examples. It goes without saying that the degree of redundancy can be set by the FEC utilization determination unit 120 based on some other method.

<3. Summary>

Thus, in the communication system according to an embodiment of the present disclosure, when packets transmitted from the transmission apparatus 100 are lost, the reception apparatus 200 recovers the lost packets by using FEC redundant packets. Further, when the FEC redundant packets are added by the transmission apparatus 100, the communication system according to an embodiment of the present disclosure uses statistical information about a duration X from a display-ready state until display collected by the reception apparatus 200 that is caused by synchronization deviation between the transmission apparatus 100 and the reception apparatus 200.

Thus, using the statistical information about the duration X collected by the reception apparatus 200, the transmission apparatus 100 can prevent too many FEC redundant packets from being added by setting the number of FEC redundant packets to be added. Therefore, when synchronization deviation has occurred between the transmission apparatus 100 and the reception apparatus 200, the communication system according to an embodiment of the present disclosure can increase recovery performance from synchronization deviation while suppressing usage of network bandwidth.

The respective steps in the processing executed by the various apparatuses described in the present disclosure do not have to be performed in chronological order according to the order described as a sequence diagram or flowchart. For example, the respective steps in the processing executed by the various apparatuses can be carried out in a different order to that described in the flowcharts, or can be carried out in parallel.

In addition, a computer program can be created that makes hardware, such as a CPU, ROM, and RAM, in the various apparatuses realize functions equivalent to the parts of the various above-described apparatuses. Still further, a storage medium on which such a computer program is stored can also be provided. Moreover, series of processes can also be realized by hardware by configuring the respective function blocks illustrated in the function block diagrams as hardware.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) A transmission apparatus including:
 a video signal transmission unit configured to transmit a video signal to another apparatus;
 a time information reception unit configured to receive, from the other apparatus, time information including a duration from reception of the video signal until a timing at which display of each frame in the video signal starts at the other apparatus; and
 a degree-of-redundancy determination unit configured to determine a degree of redundancy for the video signal transmitted from the video signal transmission unit based on the time information received by the time information reception unit.

(2) The transmission apparatus according to (1), wherein the time information reception unit is configured to receive from the other apparatus as the time information, statistical information about a duration from reception of the video signal until a timing at which display of each frame in the video signal starts at the other apparatus.

(3) The transmission apparatus according to (2), wherein the statistical information is information about a maximum value and a minimum value of a time moving average from reception of the video signal until a timing at which display of each frame in the video signal starts at the other apparatus and information about an interval between a time point at the maximum value and a time point at the minimum value.

(4) The transmission apparatus according to (3), wherein the degree-of-redundancy determination unit is configured to determine a degree of redundancy as a minimum possible value when the moving average is at a maximum value and is further configured to determine a degree of redundancy as a maximum possible value when the moving average is at a minimum value.

(5) The transmission apparatus according to (4), wherein the degree-of-redundancy determination unit is configured to linearly change the degree of redundancy between a time point at which the degree of redundancy is at a maximum value and a time point at which the degree of redundancy is at a minimum value.

(6) The transmission apparatus according to any one of (1) to (6), wherein the video signal is processed based on a plurality of lines as one unit.

(7) A transmission method including:
 transmitting a video signal to another apparatus;

receiving, from the other apparatus, time information including a duration from reception of the video signal until a timing at which display of each frame in the video signal starts at the other apparatus; and determining a degree of redundancy for the transmitted video signal based on the received time information.

(8) A computer program that makes a computer execute:

transmission of a video signal to another apparatus;

reception from the other apparatus of time information including a duration from reception of the video signal until a timing at which display of each frame in the video signal starts at the other apparatus; and determination of a degree of redundancy for the transmitted video signal based on the received time information.

(9) A reception apparatus including:

a video signal reception unit configured to receive a video signal from another apparatus;

a time measurement unit configured to measure a duration from reception of the video signal by the video signal reception unit until a timing at which display of each frame in the video signal starts; and a time information transmission unit configured, to transmit to the other apparatus, time information including information about the duration measured by the time measurement unit.

(10) The reception apparatus according to (9), wherein the time information transmission unit is configured to transmit to the other apparatus as the time information, statistical information about a duration from reception of the video signal until a timing at which display of each frame in the video signal starts.

(11) The reception apparatus according to (10), wherein the statistical information is information about a maximum value and a minimum value of a time moving average from reception of the video signal until a timing at which display of each frame in the video signal starts and information about an interval between a time point at the maximum value and a time point at the minimum value.

(12) The reception apparatus according to any one of (9) to (11), wherein, after the video signal received by the video signal reception unit has been decoded, the time measurement unit is configured to measure a duration from reception of a video signal at the video signal reception unit until a timing at which display of each frame in the video signal starts.

(13) The reception apparatus according to (9) to (12), wherein the video signal is processed based on a plurality of lines as one unit.

(14) A reception method including:

receiving a video signal from another apparatus;

measuring a duration from reception of the video signal until a timing at which display of each frame in the video signal starts; and transmitting, to the other apparatus, time information including information about the measured duration.

(15) A computer program that makes a computer execute:

reception of a video signal from another apparatus;

measurement of a duration from reception of the video signal until a timing at which display of each frame in the video signal starts; and transmission to the other apparatus of time information including information about the measured duration.

What is claimed is:

1. A transmission apparatus, comprising:
a Central Processing Unit (CPU) configured to:
   transmit a video signal to an apparatus;
   receive from the apparatus as time information, statistical information including a duration from reception of the video signal until a timing at which display of each frame in the video signal starts at the apparatus, wherein the statistical information is information about a maximum value and a minimum value of a time moving average from reception of the video signal until the timing at which display of each frame in the video signal starts at the apparatus and information about an interval between a time point at the maximum value and a time point at the minimum value; and
   determine a degree of redundancy for the transmitted video signal based on the received time information.

2. The transmission apparatus according to claim 1, wherein the CPU is further configured to determine the degree of redundancy as a minimum possible value in an event the time moving average is at the maximum value and is further configured to determine the degree of redundancy as a maximum possible value in an event the time moving average is at the minimum value.

3. The transmission apparatus according to claim 2, wherein the CPU is further configured to linearly change the degree of redundancy between the time point at which the degree of redundancy is at the maximum value and the time point at which the degree of redundancy is at the minimum value.

4. The transmission apparatus according to claim 1, wherein the video signal is processed based on a plurality of lines as one unit.

5. A transmission method, comprising:
transmitting a video signal to an apparatus;
receiving from the apparatus as time information, statistical information including a duration from reception of the video signal until a timing at which display of each frame in the video signal starts at the apparatus,
   wherein the statistical information is information about a maximum value and a minimum value of a time moving average from reception of the video signal until the timing at which display of each frame in the video signal starts at the apparatus and information about an interval between a time point at the maximum value and a time point at the minimum value; and
determining a degree of redundancy for the transmitted video signal based on the received time information.

6. A non-transitory computer-readable storage medium having stored thereon a set of instructions for causing a computer to perform operations, comprising:
transmitting a video signal to an apparatus;
receiving from the apparatus as time information, statistical information including a duration from reception of the video signal until a timing at which display of each frame in the video signal starts at the apparatus,
   wherein the statistical information is information about a maximum value and a minimum value of a time moving average from reception of the video signal until the timing at which display of each frame in the video signal starts at the apparatus and information about an interval between a time point at the maximum value and a time point at the minimum value; and determining a degree of redundancy for the transmitted video signal based on the received time information.

7. A reception apparatus, comprising:
a Central Processing Unit (CPU) configured to:
   receive a video signal from an apparatus;
   measure a duration from reception of the video signal until a timing at which display of each frame in the video signal starts; and
   transmit to the apparatus as time information, statistical information including information about the measured duration,
      wherein the statistical information is information about a maximum value and a minimum value of a time moving average from reception of the video signal until the timing at which display of each frame in the video signal starts and information about an interval between a time point at the maximum value and a time point at the minimum value.

8. The reception apparatus according to claim 7, wherein, after the received video signal has been decoded, the CPU is further configured to measure the duration from reception of the video signal until the timing at which display of each frame in the video signal starts.

9. The reception apparatus according to claim 7, wherein the video signal is processed based on a plurality of lines as one unit.

10. A reception method, comprising:
receiving a video signal from an apparatus;
measuring a duration from reception of the video signal until a timing at which display of each frame in the video signal starts; and
transmitting to the apparatus as time information, statistical information including information about the measured duration,
   wherein the statistical information is information about a maximum value and a minimum value of a time moving average from reception of the video signal until the timing at which display of each frame in the video signal starts and information about an interval between a time point at the maximum value and a time point at the minimum value.

11. A non-transitory computer-readable storage medium having stored thereon a set of instructions for causing a computer to perform operations, comprising:
receiving a video signal from an apparatus;
measuring a duration from reception of the video signal until a timing at which display of each frame in the video signal starts; and
transmitting to the apparatus as time information, statistical information including information about the measured duration,
   wherein the statistical information is information about a maximum value and a minimum value of a time moving average from reception of the video signal until the timing at which display of each frame in the video signal starts and information about an interval between a time point at the maximum value and a time point at the minimum value.

* * * * *